United States Patent
Lamps et al.

(10) Patent No.: US 9,055,899 B2
(45) Date of Patent: Jun. 16, 2015

(54) LANCING DEVICE WITH IMPROVED GUIDANCE ASSEMBLY

(75) Inventors: Greg Lamps, Smyrna, GA (US); Doug Vine, Alpharetta, GA (US); Lauren R. Pusey, Woodstock, GA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 843 days.

(21) Appl. No.: 12/909,169

(22) Filed: Oct. 21, 2010

(65) Prior Publication Data

US 2011/0098735 A1 Apr. 28, 2011

Related U.S. Application Data

(60) Provisional application No. 61/254,047, filed on Oct. 22, 2009.

(51) Int. Cl.
*A61B 17/34* (2006.01)
*A61B 5/15* (2006.01)
*A61B 5/151* (2006.01)

(52) U.S. Cl.
CPC ............ *A61B 5/1411* (2013.01); *A61B 5/15142* (2013.01); *A61B 5/15186* (2013.01)

(58) Field of Classification Search
CPC ............. A61B 5/1411; A61B 5/15142; A61B 5/15117; A61B 5/151; A61B 5/15186
USPC .................................... 606/181, 182; 600/583
See application file for complete search history.

(56) References Cited

U.S. PATENT DOCUMENTS

| | | | |
|---|---|---|---|
| 4,416,279 A | 11/1983 | Lindner et al. |
| 4,577,630 A | 3/1986 | Nitzsche et al. |
| 4,895,147 A | 1/1990 | Bodicky et al. |
| 4,924,879 A | 5/1990 | O'Brien |
| 4,976,724 A | 12/1990 | Nieto et al. |
| 5,282,822 A | 2/1994 | Macors et al. |
| 5,318,584 A | 6/1994 | Lange et al. |
| 5,423,847 A | 6/1995 | Strong et al. |
| 5,464,418 A | 11/1995 | Schraga |
| 5,554,166 A | 9/1996 | Lange et al. |

(Continued)

FOREIGN PATENT DOCUMENTS

| EP | 2050393 A1 * | 4/2009 | ............... A61B 5/14 |
|---|---|---|---|
| JP | S6238140 A | 2/1987 | |

(Continued)

OTHER PUBLICATIONS

Invitation to Pay Additional Fees for PCT/US2009/068674; Apr. 8, 2010; 8 pgs.

(Continued)

*Primary Examiner* — Thomas McEvoy
*Assistant Examiner* — Julie A Szpira
(74) *Attorney, Agent, or Firm* — Gardner Groff Greenwald & Villanueva, PC (57) ABSTRACT

A guidance mechanism for a lancing device. The guidance mechanism includes a piston having a shaft, a plurality of wings or fins extending from the shaft, a plurality of sliding engagement structures, and a lancet holder; and a chassis having a body, a plurality of longitudinal slits or cutouts, a plurality of elongated engagement structures, and an end aperture. The piston slides within the chassis, and the wings/fins engage within the slits/cutouts, allowing for linear longitudinal guidance of the piston within the chassis.

21 Claims, 6 Drawing Sheets

(56) References Cited

U.S. PATENT DOCUMENTS

| | | | |
|---|---|---|---|
| RE35,803 E | 5/1998 | Lange et al. | |
| 5,954,738 A | 9/1999 | LeVaughn et al. | |
| 5,984,940 A | 11/1999 | Davis et al. | |
| 6,045,567 A | 4/2000 | Taylor et al. | |
| 6,156,050 A | 12/2000 | Davis et al. | |
| 6,156,051 A | 12/2000 | Schraga | |
| 6,283,982 B1* | 9/2001 | Levaughn et al. | 606/172 |
| 6,322,575 B1 | 11/2001 | Schraga | |
| 6,419,661 B1 | 7/2002 | Kuhr et al. | |
| 6,602,268 B2* | 8/2003 | Kuhr et al. | 606/181 |
| 6,986,777 B2 | 1/2006 | Kim | |
| 7,105,006 B2 | 9/2006 | Shraga | |
| 7,273,484 B2 | 9/2007 | Thoes et al. | |
| 7,288,102 B2 | 10/2007 | Griffin et al. | |
| 7,655,019 B2 | 2/2010 | LeVaughn et al. | |
| 7,867,244 B2 | 1/2011 | Lathrop et al. | |
| 7,914,547 B2 | 3/2011 | Curry et al. | |
| 7,955,348 B2 | 6/2011 | Trissel et al. | |
| 2002/0029058 A1* | 3/2002 | Levaughn et al. | 606/181 |
| 2003/0109895 A1* | 6/2003 | Taylor et al. | 606/181 |
| 2004/0098008 A1* | 5/2004 | Taylor et al. | 606/181 |
| 2004/0260326 A1* | 12/2004 | Lipoma et al. | 606/182 |
| 2005/0125019 A1 | 6/2005 | Kudrna et al. | |
| 2005/0245953 A1* | 11/2005 | Cote | 606/181 |
| 2005/0288699 A1* | 12/2005 | Schraga | 606/181 |
| 2006/0100656 A1* | 5/2006 | Olson et al. | 606/181 |
| 2006/0247671 A1* | 11/2006 | LeVaughn | 606/182 |
| 2006/0264996 A1 | 11/2006 | LeVaughn et al. | |
| 2007/0173874 A1 | 7/2007 | Uschold et al. | |
| 2007/0288047 A1 | 12/2007 | Thoes et al. | |
| 2008/0082117 A1 | 4/2008 | Ruf | |
| 2009/0264911 A1* | 10/2009 | Kim | 606/182 |
| 2010/0160942 A1 | 6/2010 | Lamps et al. | |

FOREIGN PATENT DOCUMENTS

| | | |
|---|---|---|
| JP | 2009525065 A | 7/2009 |
| WO | 2007123509 A2 | 11/2007 |
| WO | 2010080584 A1 | 7/2010 |
| WO | 2010080585 A1 | 7/2010 |
| WO | 2011050142 A1 | 4/2011 |

OTHER PUBLICATIONS

International Search Report and Written Opinion for PCT/US2009/068674; Jun. 9, 2010; 18 pgs.

Invitation to Pay Additional Fees for PCT/US2009/068671; Apr. 8, 2010; 8 pgs.

International Search Report and Written Opinion for PCT/US2009/068671; Jun. 9, 2010; 18 pgs.

International Search Report and Written Opinion for PCT/US2010/053506; Feb. 4, 2011; 15 pgs.

Japanese Office Action for Japanese Patent Application No. 2012-535359; Jun. 24, 2014; 4 pgs.

* cited by examiner

LANCING DEVICE WITH IMPROVED GUIDANCE ASSEMBLY

CROSS-REFERENCE TO RELATED APPLICATION

This application claims the benefit of U.S. Provisional Patent Application Ser. No. 61/254,047, filed Oct. 22, 2009, the entirety of which is hereby incorporated herein by reference for all purposes.

TECHNICAL FIELD

The present invention relates generally to the field of medical devices, and more particularly to lancing devices and guidance mechanisms for a lancing device.

BACKGROUND

Many medical procedures require puncturing of the skin, and sometimes underlying tissues, of an animal or human subject. For example, a sharp lancet tip is commonly used to puncture the subject's skin at a lancing site to obtain a sample of blood or other body fluid, as for example in blood glucose monitoring by diabetics and in blood typing and screening applications. A lancing device having a spring-loaded or otherwise energized drive mechanism is often used to carry the lancet along a path of travel, between a retracted or shielded position and an extended position wherein the lancet tip punctures the skin.

Some known lancing devices seek to guide the path of the lancet by positioning a lancet holder between two partial shells or within a tube-shaped carrier. The partial shell method takes two (or more) shells and fastens them together using adhesives, ultrasonic welding, crush fits, snaps, screws, or other fastening methods. Unfortunately, in addition to the dimensional variations (tolerances) inherent to the manufacturing process used to make the shells there is also a tolerance associated with the fastening method. This typically results in a loose guidance of the lancet holder (as too tight of a fit will detrimentally create drag on the lancet holder slowing it down). In order to surmount the issues with the assembled shell method, manufacturers have attempted to mold a 'tube' that is monolithic and therefore eliminates the assembly tolerances. However, the tube suffers from the requirement to have draft on the interior surfaces in order to successfully de-mold the part, which can also detrimentally affect lancet guidance.

It is to the provision of a lancing device having an improved guidance mechanism that the present invention is primarily directed.

SUMMARY

In example embodiments, the present invention relates to an improved lancing device and to a guidance mechanism for use with a lancing device. The guidance mechanism reduces lateral motion of the lancet tip, for example side-to-side "wobble" or twisting motion, and maintains a straight linear or axial lancing stroke to reduce the sensation of pain to the subject.

In example embodiments, the guidance mechanism comprises a piston and a guidance chassis. The piston comprises a body, a plurality of wings or fins, a plurality of sliding engagement structures, and a lancet holder or receiver. The chassis comprises a body, a plurality of longitudinal slits or channels, a plurality of guidance surfaces, and an end opening or aperture. The piston slides translationally within the chassis, with its wings/fins engaged in the slits/cutouts, allowing for longitudinal movement of the piston within the chassis.

In another aspect, the invention relates to a guidance mechanism for a lancing device. The guidance mechanism preferably includes a piston having a shaft, a plurality of fins extending from the shaft, a plurality of sliding engagement structures at the distal ends of the fins, and a lancet holder. The guidance mechanism preferably also includes a chassis comprising an elongate hollow chamber bounded by sidewalls, the sidewalls having guidance channels formed therein with engagement surfaces along the guidance channels. The piston slides freely within the hollow chamber of the chassis with the fins of the piston received in the guidance channels of the chassis, and with the sliding engagement structures of the piston aligned with the engagement surfaces of the chassis.

In still another aspect, the invention relates to a lancing device guidance mechanism including a housing and a lancet mounted for translation relative to the housing along a linear path of travel. The housing preferably defines a linear slot extending parallel to the lancet's linear path of travel and including a housing guidance surface along the slot. The lancet preferably has a wing extending therefrom with a lancet guidance surface thereon, wherein the wing extends through the slot, and the lancet guidance surface slides along the housing guidance surface to constrain the lancet to translational movement along its linear path of travel.

In another aspect, the invention relates to a lancet for use in combination with a lancing device guidance mechanism. The lancing device guidance mechanism preferably includes a housing having a linear slot formed therein, a carrier platform, and a spring coupled between the housing and the carrier platform. The lancet preferably includes a lancet body, a sharp lancet tip projecting in an axial direction from the lancet body, a wing extending from the lancet body in a transverse direction generally perpendicular to the axial direction, a lancet guidance surface extending from the wing in a direction oblique to the transverse direction, and a coupling for releasable attachment to the carrier platform. The wing is adapted to extend through the slot of the housing and position the lancet guidance surface in sliding relation along a housing guidance surface extending along the slot in the housing.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
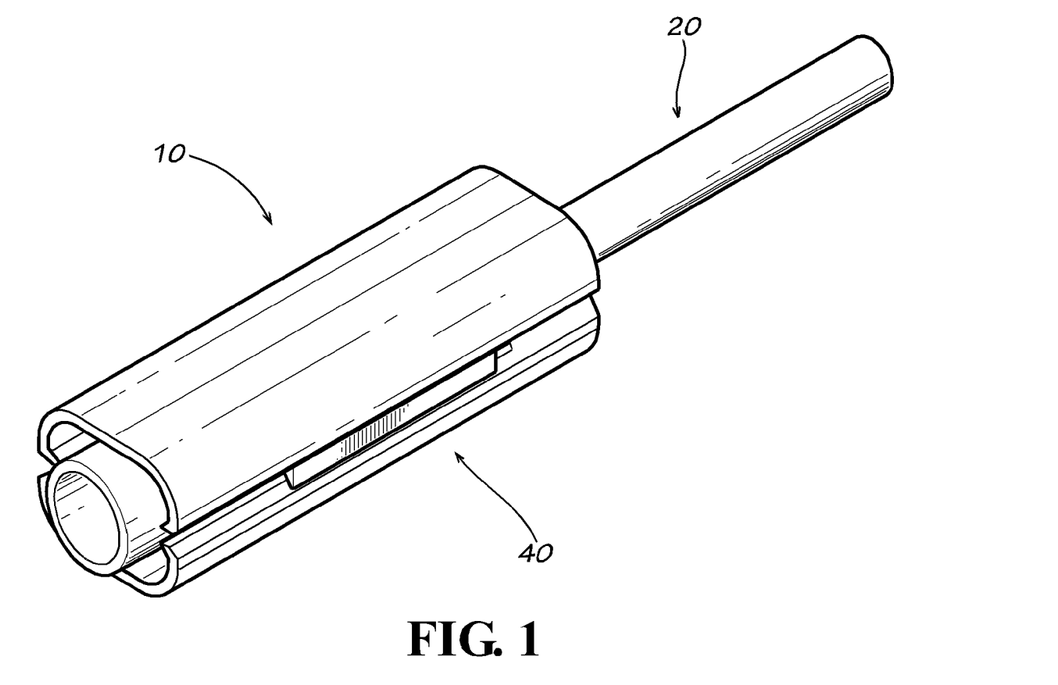
FIG. 1 is a perspective view of a lancing device guidance mechanism according to an example embodiment of the present invention.
Figure 2:
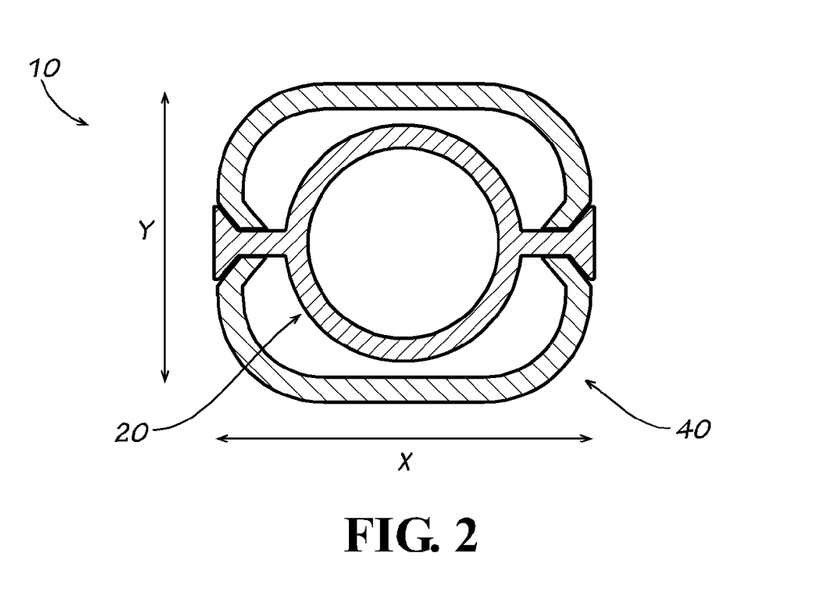
FIG. 2 is a front end view of the lancing device guidance mechanism of FIG. 1.

With reference now to the drawing figures, wherein like reference numbers represent corresponding parts throughout the several views, FIGS. 1-2 show a guidance mechanism 10 for a lancing device. The guidance mechanism 10 generally comprises a piston 20 and a guidance chassis or housing 40. The components of the guidance mechanism 10 can be fabricated from plastics, metals, ceramics, and/or other materials; and can be formed by injection molding, reaction injection molding, die casting, machining, extruding, sintering, casting, thermoforming, and/or other manufacturing techniques.

Figure 3:
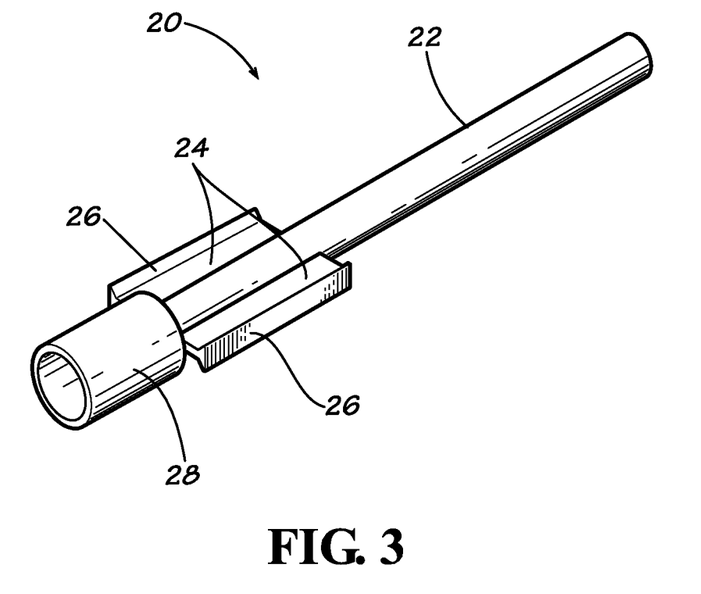
FIG. 3 is a perspective view of a piston component of the lancing device guidance mechanism of FIG. 1.
Figure 4:
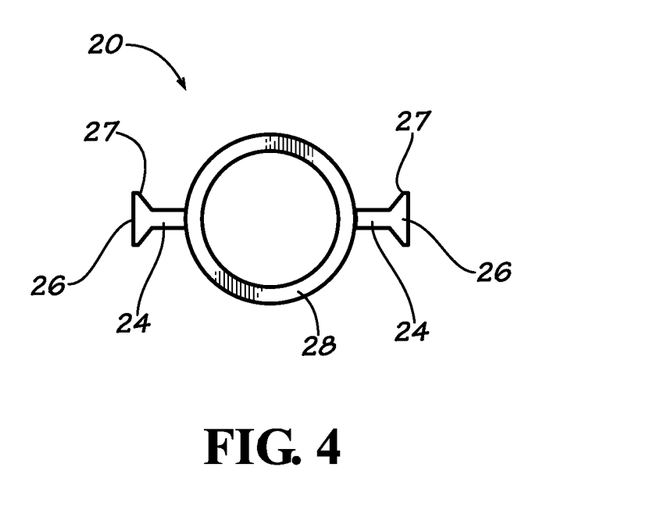
FIG. 4 is a front end view of the piston of FIG. 3.

As seen in more detail in FIGS. 3-4, the piston 20 comprises a shaft 22, a plurality of wings or fins 24 projecting laterally or radially from the shaft, a plurality of sliding flanges or engagement structures 26 at the distal or free ends of the wings/fins 24, and a lancet holder or carrier 28 for releasably engaging a disposable lancet. The shaft 22 is a generally elongate cylindrical or tubular structure, defining a lengthwise axis. Optionally, the shaft 22 can have a circular, rectangular, or otherwise configured cross sectional profile, and can be hollow, solid, or a combination thereof. The plurality of wings or fins 24 are integrally formed with or otherwise attached to the shaft 22. In the depicted embodiment, there are two wings/fins 24 located at diametrically opposed locations near the front end of the shaft 22. In alternate embodiments, three or more wings/fins 24 may be provided, and the wings/fins 24 can be spaced at different locations around the shaft 22, depending on the design of the guidance mechanism 10. The wings/fins 24 are generally flat and thin planar structures, and extend outward from the shaft 22, aligned parallel with the lengthwise axis of the shaft 22.

A sliding engagement structure or bearing surface 26 is located along the distal end of each of the wings/fins 24. In the depicted embodiment, the sliding engagement structures 26 comprise triangular or trapezoidal flanges having "dovetail" cross-sectional profiles. The inwardly directed (i.e., facing toward the shaft 22) inclined faces of each dovetail engagement structure 26 defines first and second tapered guidance surfaces 27 that slidingly engage cooperating contact faces of the chassis 40, as described below, the first and second tapered guidance surfaces being oriented generally perpendicular or at an obtuse angle to one another. The dovetail engagement structures 26 can optionally extend along the entire length of the distal ends of the wings/fins 24, as depicted in the example embodiment, or they can extend a shortened distance along a portion of the distal ends of the wings/fins 24.

Positioned at the front end of the shaft 22 is the lancet holder 28. The lancet holder 28 of the depicted embodiment comprises a hollow cylinder with an open front receiver end for receiving and frictionally engaging a lancet of corresponding dimension by a friction/interference fit. In alternate embodiments, the lancet is retained in the receiver by one or more releasable couplings, or is permanently attached or integrally formed with the shaft as in a single-use disposable lancing device. The rear end of the lancet holder 28 is connected to the shaft 22 or integrally formed therewith, and the central axis of the lancet holder 28 is generally aligned with the lengthwise axis of the shaft 22.

Figure 5:
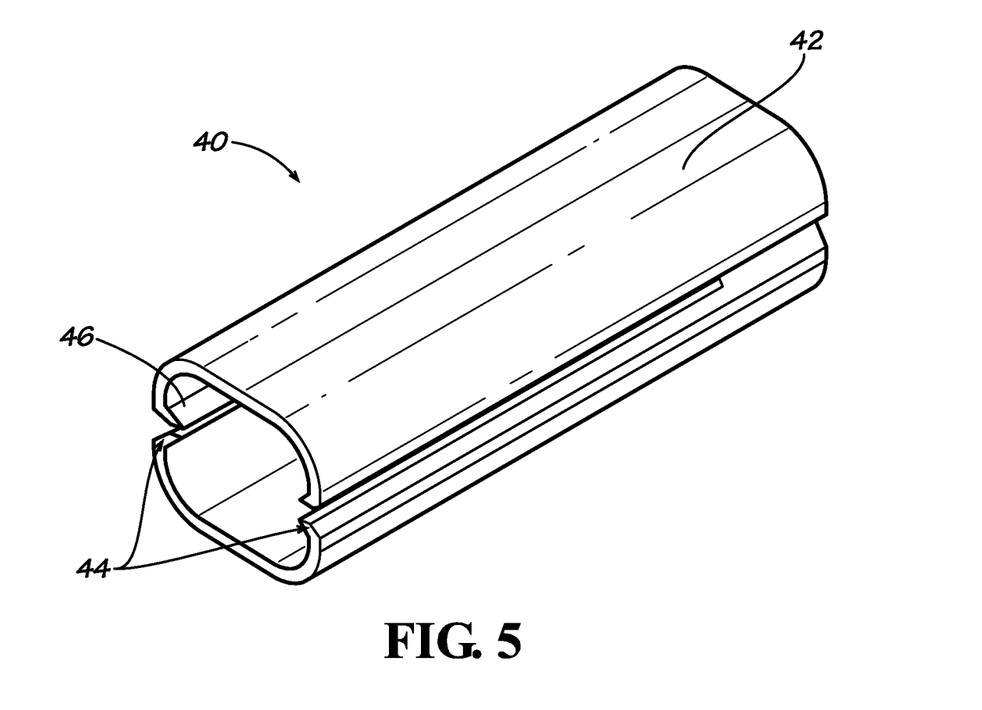
FIG. 5 is a perspective view of a guidance chassis component of the lancing device guidance mechanism of FIG. 1.
Figure 6:
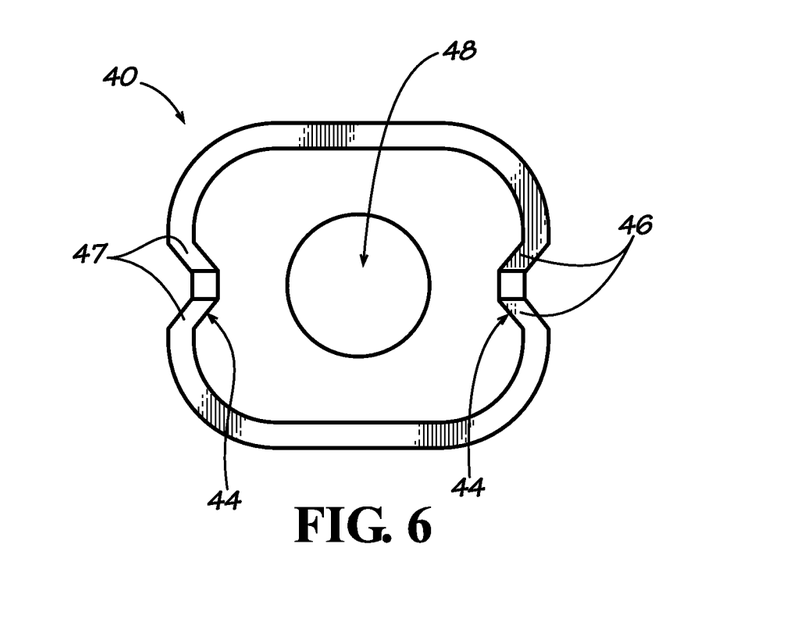
FIG. 6 is a front end view of the guidance chassis of FIG. 5.

As seen in FIGS. 5-6, the guidance chassis 40 comprises a chassis body 42, a plurality of slits/cutouts or guidance channels 44, a plurality of elongated engagement surfaces 46, an open front end, and a rear aperture 48. In the depicted embodiment, the chassis 40 defines a generally rectangular cross sectional profile with rounded corners. The chassis 40 is generally hollow and elongate, having a central axis that coincides with the lengthwise axis of the shaft when the device is assembled. The guidance channels 44 extend along one or more of the peripheral walls of the chassis 40, parallel with the central axis. In the depicted embodiment, there are two slits/cutouts 44 located on opposing lateral sides that extend from the open front face of the chassis 40 and extend longitudinally along the side walls of the chassis 40 extending along at least a portion of the length of the chassis 40. In the depicted embodiment, the slits 44 form channels extending from the open front end of the chassis at least halfway, and preferably at least about 75% of the length of the chassis.

In the depicted embodiment of FIGS. 1-6, the engagement surfaces 46 comprise inwardly recessed tracks 47 arranged in pairs along opposite sides of the guidance channels 44. The tracks 47 of engagement surfaces 46 extend inwardly towards the central axis of the chassis 40, and have outwardly facing contact surfaces that are inclined at an angle that generally corresponds to or matches the tapered inwardly facing guidance surfaces 27 of the dovetail engagement structures 26 of the piston 20. In alternate embodiments, the guidance surfaces of the piston and the engagement surfaces of the chassis can comprise planar and/or curved surfaces. For example, a planar guidance surface and a correspondingly oriented planar engagement surface can provide contact across a two-dimensional plane of contact; a curved guidance surface and a correspondingly curved engagement surface can provide contact across a three-dimensional surface of contact; or a curved guidance surface and a planar engagement surface (or vice-versa) can provide contact along a line of contact. The transverse spacing between the tracks 47 on one side of the chassis and those on the opposite side of the chassis corresponds with the spacing between the guidance surfaces 27 of the piston, as determined by the length of the wings/fins 24. The sliding contact and interaction between the tapered guidance surfaces 27 and the tracks 47 allows a smooth sliding motion of the piston 20 within the chassis while maintaining precise linear and axial path of travel along the lancing stroke as explained in further detail below. A rear aperture 48 is formed in the back end of the chassis 40, positioned and sized to receive the shaft 22 of the piston 20 therethrough with a free running fit.

In use, the piston 20 is assembled into the chassis 40 with the shaft 22 of the piston extending through the aperture 48 in the back of the chassis, and with the wings/fins 24 of the piston extending through the guidance channels 44 of the chassis. The dovetail engagement structures 26 of the piston are positioned between the engagement surfaces 46 of the chassis, with guidance surfaces 27 of the piston sliding along the tracks 47 of the chassis. This freely sliding contact between the piston 20 and the chassis 40 constrains the lancing stroke along a linear path. Alignment of the complementary angled guidance surfaces 27 of the dovetail engagement structures 26 with the tracks 47 resists wobbling or twisting motion in either the first lateral direction (horizontal) defined by the axis X in FIG. 2, or the second perpendicular lateral direction (vertical) defined by the axis Y.

The reduction in lateral movement during the lancing stroke provides for a cleaner puncture wound on the surface of the skin without significant sideways tearing of tissue, and therefore less pain perceived by the subject. Additionally, the manufacturing of the guidance mechanism 10 prevents the introduction of dimensional tolerances present in most previously known guidance mechanisms for lancing devices.

Figure 7A:
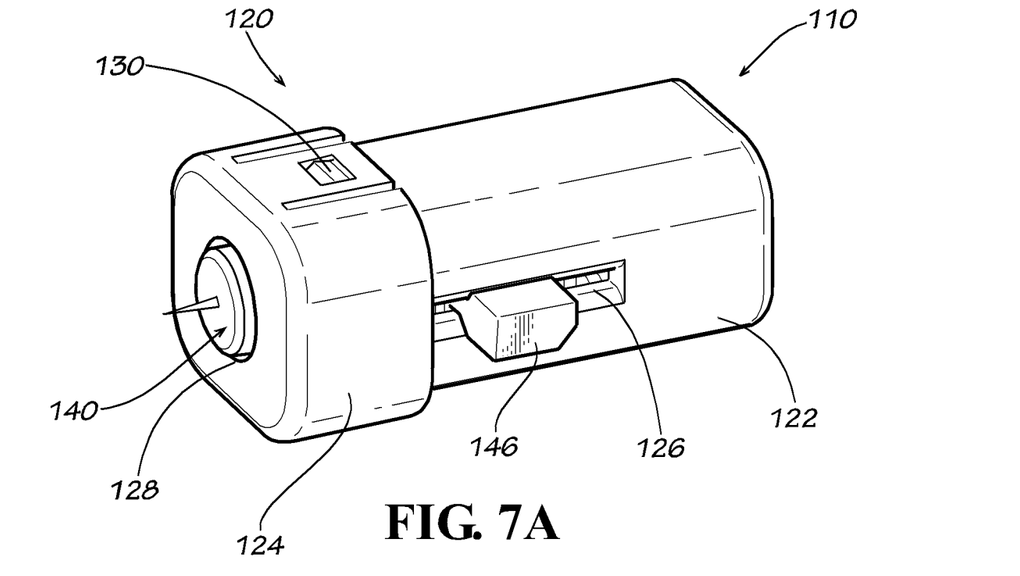
FIGS. 7A and 7B show a lancing device according to another example embodiment of the invention, in perspective and cross-sectional views respectively.
Figure 7B:
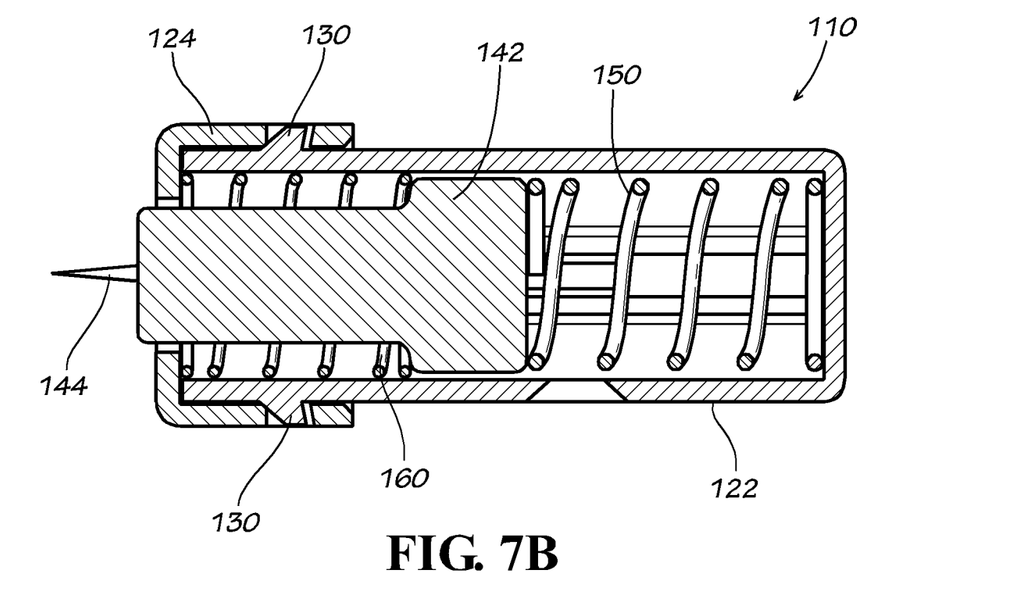

FIGS. 7A and 7B show an alternate embodiment of a lancing device guidance system 110 according to an example form of the invention. The lancing device guidance system 110 includes a housing 120 comprising a body portion 122 having an open front end and a closed back end, and a cap 124, the housing and the cap bounding an enclosed chamber when assembled. One or more slot(s) 126 extend lengthwise along the body 122. A lancet opening 128 is formed in the end face of the cap 124. An opposed pair of snap couplings 130 retain the cap 124 on the body 122. A lancet 140 is translationally mounted within the chamber of the housing 120. The lancet 140 comprises a lancet body 142 having a sharp lancet tip 144 projecting axially from a front face thereof, and one or more actuator wing(s) 146 extending transversely from a side portion thereof. A drive spring 150 is provided in compression between the closed back end of the housing 120 and the rear face of the lancet to bias and propel the lancet in a forward direction to a lancing position wherein the sharp lancet tip 144 extends outwardly of the lancing device to lance the subject's skin at a sampling site. A return spring 160 is provided in compression between the inside face of the cap 124 and a front shoulder surface of the lancet body 122, to bias and retract the lancet to a retracted position shielded within the lancing device after lancing. The one or more actuator wing(s) 146 extend through the slot(s) 126 and have inclined contact faces at their free ends for sliding contact and guidance in conjunction with corresponding guidance surfaces of the housing body along the sides of the slot(s) 126, in similar fashion to that described above. So configured, the system 110 may comprise a stand-alone single-use lancing device, or alternatively may comprise a replaceable lancet/drive/guidance cartridge for insertion and use with an unshown lancing device.

Figure 8A:
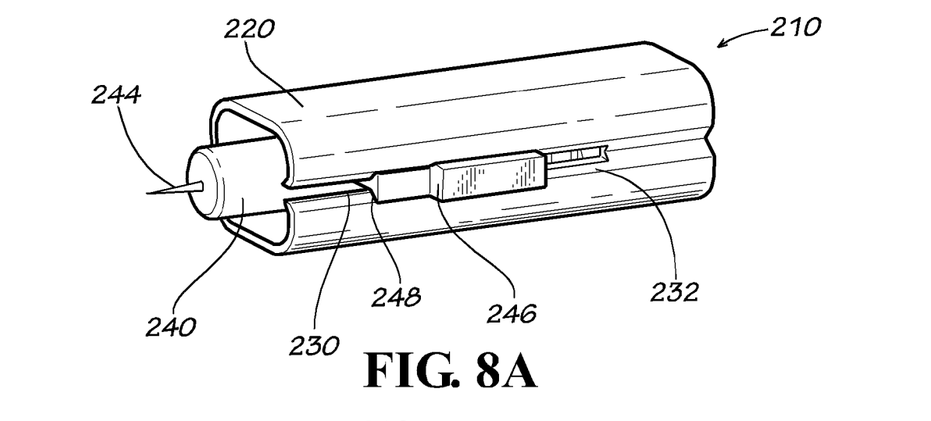
FIGS. 8A, 8B and 8C show a lancing device according to yet another example embodiment of the invention, in perspective, hidden line, and cross-sectional views respectively.
Figure 8B:
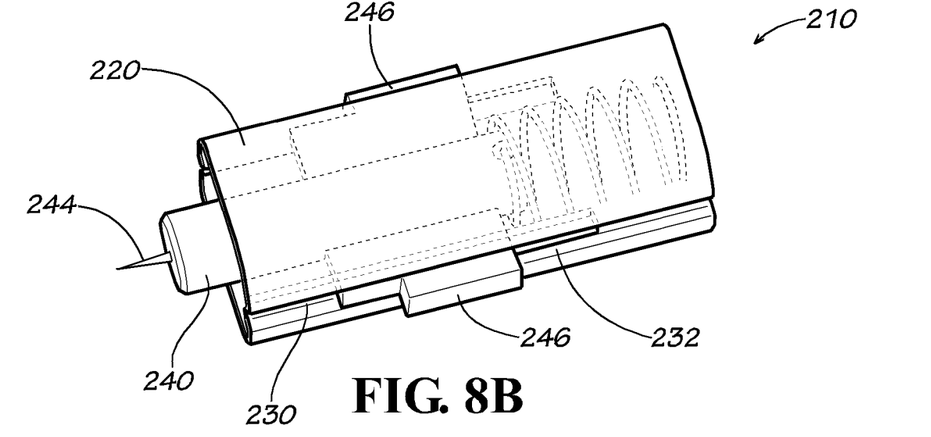
Figure 8C:
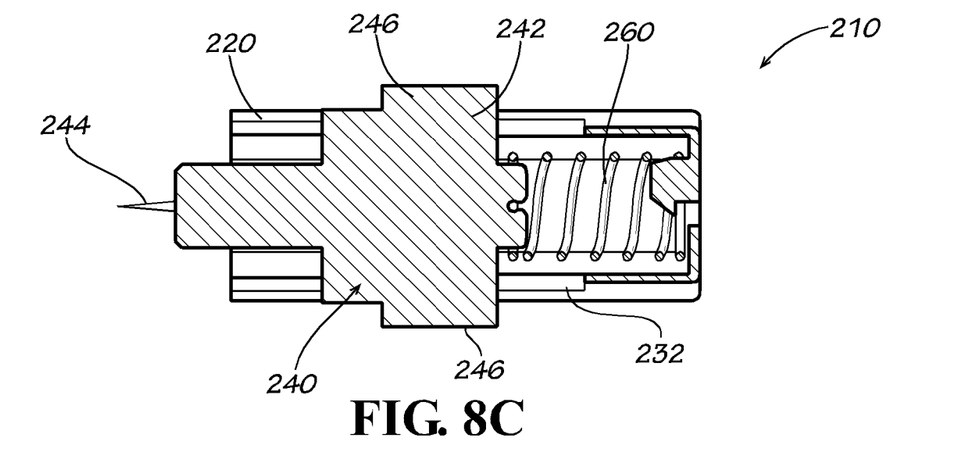

FIGS. 8A, 8B and 8C show another alternate embodiment of a lancing device guidance system 210 according to an example form of the invention. The lancing device guidance system 210 includes a housing 220 having an open front end and a closed back end, with slots 230 along opposite sides of the housing extending from the front end and along a portion of the length of the housing. Similar to the above described embodiments, the housing has guidance surfaces 232 extending along the length of the slots 230. A lancet 240 comprises a lancet body 242, a sharp lancet tip 244 projecting from a forward face of the lancet body, and a pair of wings 246 extending laterally from opposite sides of the lancet body. The wings 246 extend through the slots 230 and have obliquely inclined guidance surfaces 248 corresponding to the guidance surfaces 232 along the slots 230 of the housing to guide the lancet 240 along a linear lancing stroke. The wings 246 may be integrally molded as a unitary part of the lancet body 242, or may be affixed to the body by adhesive, friction fit, ultrasonic welding, or other attachment means. A single drive/return coil spring 260 has a distal end connected to the back end of the housing 220, and a proximal end connected to the lancet 240 to bias and propel the lancet along a linear lancing stroke, guided by the interaction between the guidance surfaces 248 of the lancet and the guidance surfaces 232 of the housing 220.

Figures 9A, 9B:
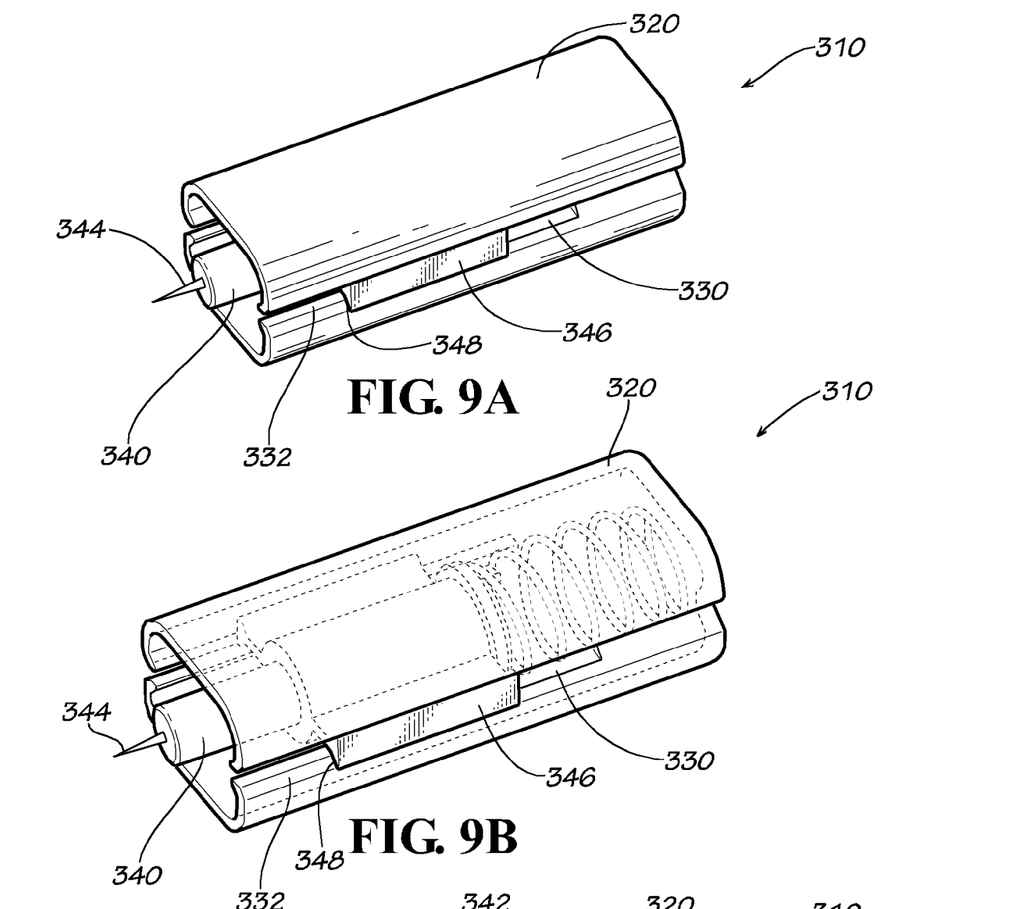
FIGS. 9A, 9B and 9C show a lancing device according to still another example embodiment of the invention, in perspective, hidden line, and cross-sectional views respectively.
Figure 9C:
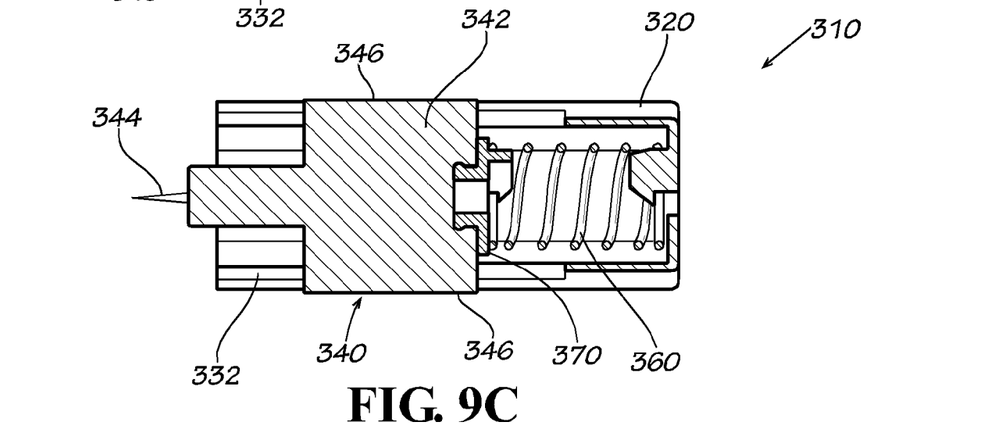

FIGS. 9A, 9B and 9C show another alternate embodiment of a lancing device guidance system 310 according to an example form of the invention. The lancing device guidance system 310 includes a housing 320 having an open front end and a closed back end, with slots 330 along opposite sides of the housing extending from the front end and along a portion of the length of the housing. Similar to the above described embodiments, the housing has guidance surfaces 332 extending along the length of the slots 330. A lancet 340 comprises a lancet body 342, a sharp lancet tip 344 projecting from a forward face of the lancet body, and a pair of wings 346 extending laterally from opposite sides of the lancet body. The wings 346 extend through the slots 330 and have obliquely inclined guidance surfaces 348 corresponding to the guidance surfaces 332 along the slots 330 of the housing to guide the lancet 340 along a linear lancing stroke. A single drive/return coil spring 360 has a distal end connected to the back end of the housing 320, and a proximal end connected to a carrier platform 370. The lancet 340 includes a coupling for releasably engaging and detaching from the carrier platform 370, to enable lancet replacement, while the carrier platform remains permanently attached to the spring 360. The coupling may comprise, for example, a mortised receiver in the rear face of the lancet body, and a resilient flanged hub projecting from the carrier platform for releasable engagement with the receiver. In this manner, the lancet may be a disposable component for insertion into and removal from a reusable lancing device guidance system.

While the invention has been described with reference to preferred and example embodiments, it will be understood by those skilled in the art that a variety of modifications, additions and deletions are within the scope of the invention, as defined by the following claims.

What is claimed is:

1. A guidance mechanism for a lancing device, said guidance mechanism comprising:
   a piston comprising a shaft, a plurality of fins extending from the shaft, a plurality of dovetail-tapered sliding engagement surfaces at the distal ends of the fins, and a lancet holder; and a chassis comprising an elongate hollow chamber bounded by sidewalls, the sidewalls having guidance channels formed therein with tapered engagement surfaces along the guidance channels;

wherein the piston slides freely within the hollow chamber of the chassis with the fins of the piston received in the guidance channels of the chassis, and with the dovetail-tapered sliding engagement surfaces of the piston aligned with the tapered engagement surfaces of the chassis, and wherein the plurality of fins extend through the channels such that the fins are exposed exteriorly of the chassis.

2. The guidance mechanism of claim 1, wherein the shaft of the piston extends through a rear aperture of the chassis.

3. The guidance mechanism of claim 1, wherein the plurality of fins comprise first and second fins extending radially outward from diametrically opposite sides of the shaft.

4. A lancing device comprising the guidance mechanism of claim 1, and means for propelling the piston along a lancing stroke.

5. The lancing device of claim 4, wherein the means for propelling the piston along a lancing stroke comprises a spring-driven mechanism.

6. A lancing device guidance mechanism comprising a housing and a lancet mounted for translation relative to the housing along a linear path of travel, the housing defining a linear slot extending parallel to the lancet's linear path of travel and comprising a tapered housing guidance surface along the slot, the lancet having a wing extending therefrom having a dovetail-tapered lancet guidance surface thereon, wherein the wing extends through the slot such that the wing is at least partially exposed along an exterior portion of the housing, and the dovetail-tapered lancet guidance surface slides along the tapered housing guidance surface to constrain the lancet to translational movement along its linear path of travel.

7. The lancing device guidance mechanism of claim 6, wherein the lancet is advanced along its linear path of travel in at least a first direction by a first spring.

8. The lancing device guidance mechanism of claim 7, wherein the first spring advances the lancet in a first direction and retracts the lancet in a second direction opposite the first direction.

9. The lancing device guidance mechanism of claim 7, further comprising a second spring biasing the lancet in opposition to the first spring to retract the lancet.

10. The lancing device guidance mechanism of claim 7, wherein the lancet is directly coupled to the spring.

11. The lancing device guidance mechanism of claim 7, wherein the lancet is engaged by a lancet carrier coupled to the spring.

12. The lancing device guidance mechanism of claim 7, wherein the lancet is engaged by a carrier platform coupled to the spring.

13. The lancing device guidance mechanism of claim 6, wherein the dovetail-tapered lancet guidance surface and the tapered housing guidance surface are angularly inclined and confront along a plane oblique to the lancet's linear path of travel.

14. The lancing device guidance mechanism of claim 13, wherein the dovetail-tapered lancet guidance surface comprises a profile having first and second inwardly-directed angularly inclined faces confronting first and second outwardly-directed angularly inclined faces of the housing extending along opposite sides of the slot.

15. The lancing device guidance mechanism of claim 6, wherein the housing defines a second slot extending parallel to the lancet's linear path of travel and opposite from the first slot.

16. The lancing device guidance mechanism of claim 6, comprising a single-use lancing device.

17. The lancing device guidance mechanism of claim 6, comprising a replaceable cartridge for insertion into and removal from a lancing device.

18. A lancet for use in combination with a lancing device guidance mechanism, the lancing device guidance mechanism including a housing having a linear slot formed therein, a carrier platform, and a spring coupled between the housing and the carrier platform, the lancet comprising:

a lancet body;

a sharp lancet tip projecting in an axial direction from the lancet body;

a wing extending from the lancet body in a transverse direction generally perpendicular to the axial direction;

a dovetail-tapered lancet guidance surface extending from the wing obliquely to the transverse direction; and a coupling for releasable attachment to the carrier platform;

wherein the wing is adapted to extend through the slot such that at least a portion thereof is exposed about an exterior portion of the housing, and position the dovetail-tapered lancet guidance surface in sliding relation along a correspondingly tapered housing guidance surface extending along the slot in the housing.

19. The lancet of claim 18, wherein the wing comprises a first wing, the lancet further comprising a second wing extending from the lancet body opposite the first wing.

20. The lancet of claim 18, wherein the dovetail-tapered lancet guidance surface comprises a trapezoidal profile at the free end of the wing.

21. The lancet of claim 18, wherein the coupling comprises a receiver opening formed in a rear face of the lancet body.

* * * * *